United States Patent [19]

Gatten et al.

[11] Patent Number: 4,461,166
[45] Date of Patent: Jul. 24, 1984

[54] DYNAMIC CURRENT DRIVE METHOD FOR POWERING THERMAL CONDUCTIVITY DETECTORS

[75] Inventors: Ronald A. Gatten, Placerville; Paul L. Patterson, Walnut Creek, both of Calif.

[73] Assignee: Delta Associates, Inc., San Jose, Calif.

[21] Appl. No.: 352,657

[22] Filed: Feb. 26, 1982

[51] Int. Cl.³ .................................... G01N 25/36
[52] U.S. Cl. ........................................ 73/27 R
[58] Field of Search ............... 73/27 R, 204; 374/173; 323/366, 369

[56] References Cited

U.S. PATENT DOCUMENTS

| | | | |
|---|---|---|---|
| 3,864,959 | 2/1975 | MacDonald | 73/27 R |
| 4,000,454 | 12/1976 | Brakl | 323/366 |
| 4,057,755 | 11/1977 | Piesche | 73/27 R |

Primary Examiner—Stephen A. Kreitman
Attorney, Agent, or Firm—Thomas E. Schatzel

[57] ABSTRACT

A gas stream detection apparatus having a balanced resistive bridge network enclosed within a housing and an electronic power supply for driving the bridge network. The power supply includes a voltage source feeding a voltage-to-current converter with two differential inputs, a current sensing resistor between the converter and bridge, twin feedback paths to the differential inputs, and a large source resistance connected to the voltage source and in parallel with a smaller source resistance, each connected to separate differential inputs. The resistance R of two bridge filaments increase by $\Delta R$ when exposed to high sample gas concentration causing variations in a current I supplied to the bridge. As $\Delta R$ increases, a bridge output voltage $E_O$ decreases. The dependence of current I on $\Delta R$ depends on circuit parameters. The difference between the source resistances permits the voltage source to be non-constant and load dependent. The source output polarity opposes the feedback polarity and under steady state a fixed current I exists. When sample concentration increases, the feedback input decreases causing current I to increase which restores detector sensitivity and provides a linear output voltage response $E_O$.

24 Claims, 4 Drawing Figures

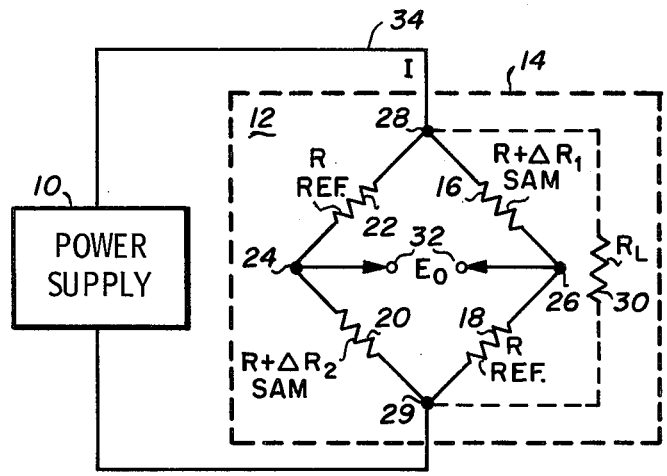
Fig_1
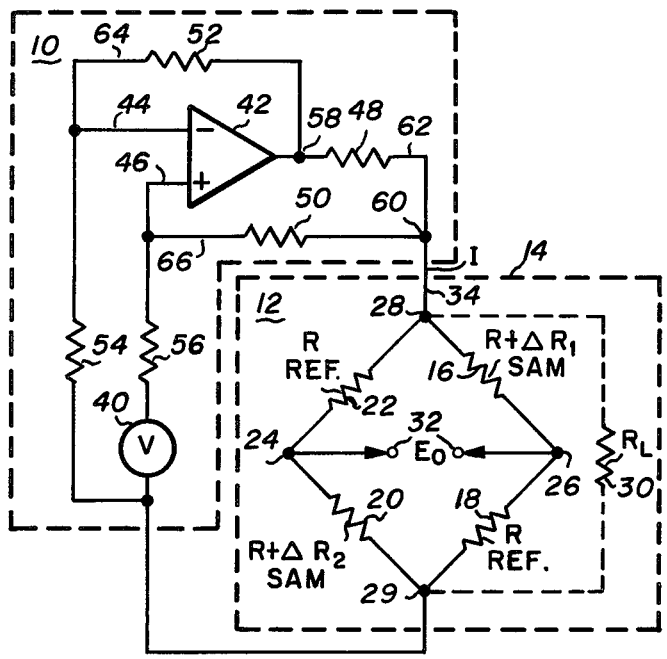
Fig_2

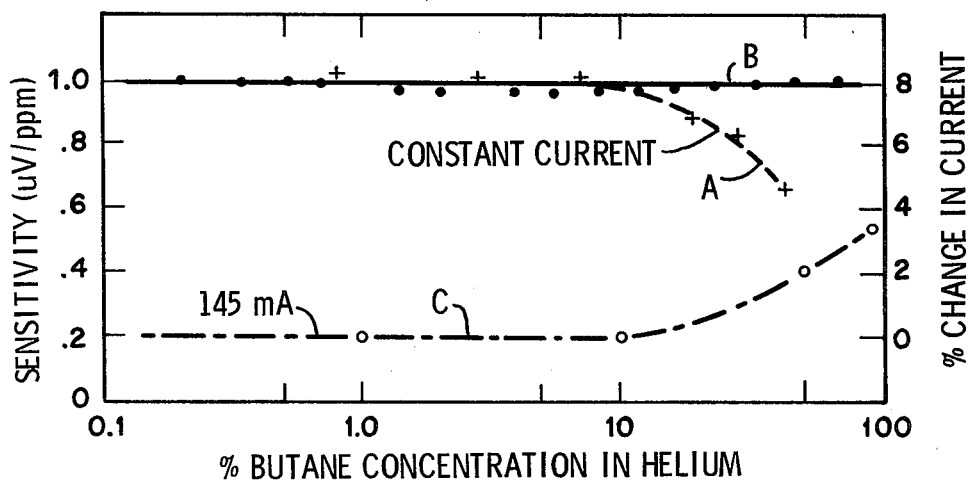
Fig_3
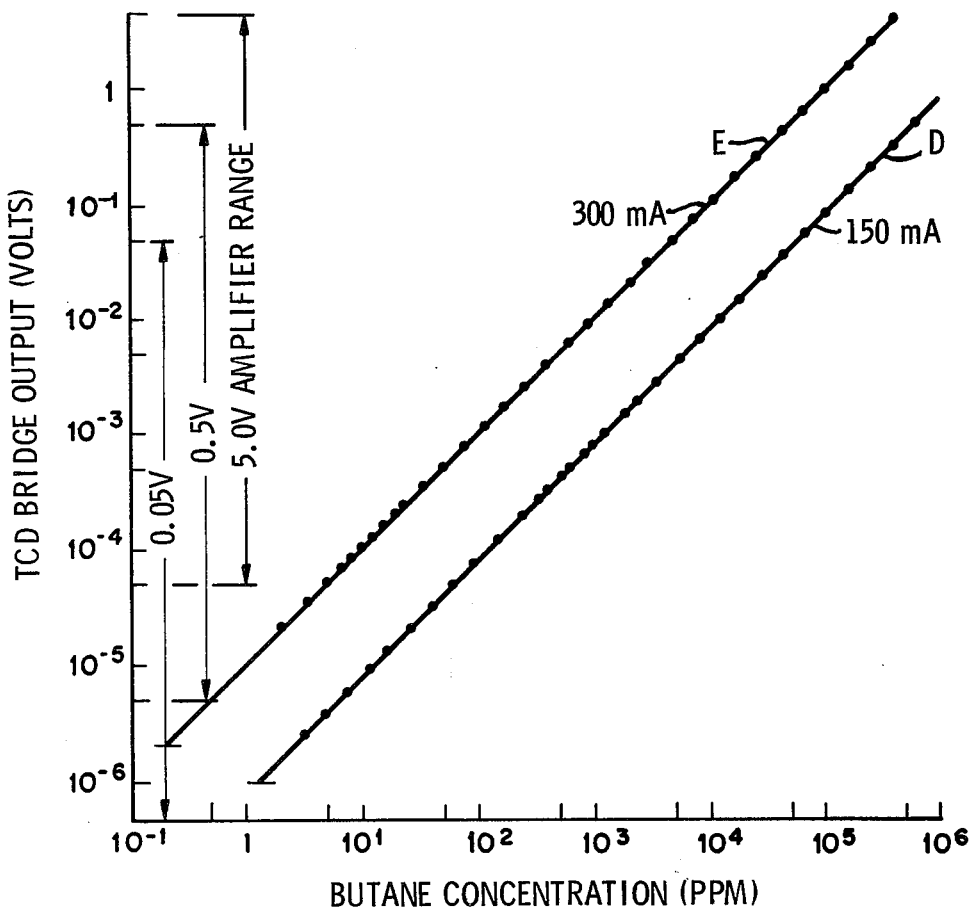
Fig_4

DYNAMIC CURRENT DRIVE METHOD FOR POWERING THERMAL CONDUCTIVITY DETECTORS

BACKGROUND OF THE INVENTION

1. Field of the Invention

The present invention relates generally to gas chromatography and more particularly to a thermal conductivity detection device wherein a change in sample gas stream composition is identified pursuant to the measurement of electrical variations in electrical circuitry.

2. Description of the Prior Art

In detecting changes in gas stream composition, a detection device sensitive to the thermal conductivity of the sample gas is normally used. The sensitive component of the detector is a resistance filament located within a sample chamber. An electrical current is passed through the filament resulting in a filament equilibrium temperature above that of the chamber wall and that filament temperature is determined by the thermal balance of the electrical heat input to the filament minus the thermal losses of the filament. Design considerations permit the primary thermal loss of the filament to be by thermal conduction of heat through the surrounding gas stream within the sample chamber. Because the thermal conductivity of a gas stream is dependent upon the chemical composition of the gas, the equilibrium temperature of the filament is also dependent upon the composition of the gas. Therefore, thermal conductivity detectors identify changes in gas composition by sensing temperature changes in the resistance filament.

The thermal conductivity theory can be realized because a unique relationship exists between the temperature of the resistance filament and the electrical resistance of the resistance filament. The filament electrical resistance is sensed by including this filament as one component of a balanced resistance network known as a Wheatstone bridge. An electrical current is supplied to the resistance components of the bridge which causes a reduction in potential difference across and an increase in temperature of each resistance component. Any resistance imbalance of the resistance filaments can be determined by detecting any voltage imbalance measured at the bridge network midpoint.

Normally, two resistance filaments are exposed to a mixture of sample gas and a reference gas of fixed composition and two resistance filaments are exposed only to the reference gas. The reference gas usually has a higher thermal conductivity than the mixture and as the concentration of the sample gas increases, the thermal conductivity of the mixture decreases causing the temperature and electrical resistance of the exposed resistance filaments to increase. The resulting voltage imbalance of the Wheatstone bridge caused by the increase in resistance of the filament represents the difference in thermal conductivity between the sample gas and the reference gas. The thermal conductivity detector's sensitivity to differences in thermal conductivity increases with increasing current supplied to the bridge.

Four common methods are used to power the detector. One method applies a fixed voltage across the detector and a second method applies a constant current to the detector. In both methods, the detector output signal is the voltage imbalance at the bridge midpoint. A third method is the constant temperature method which maintains a balanced bridge by use of feedback voltage control which is the output signal. The fourth method is a constant mean temperature technique which utilizes a bridge circuit within a second bridge circuit and feedback control. Its output signal is the voltage imbalance across the inner bridge. All methods of powering the detector produce response characteristics which are output signals linearly proportional to the sample concentration only at low sample concentrations. The non-linear response of the thermal conductivity detector exists because the theoretical relationship between the detector output voltage and sample concentration is not a linear relationship. In order for the detector to be an ideal linear device, the following relationship must exist. The detector output voltage must be a linear function of the change in resistance of the resistance filaments exposed to the sample gas, which exist for the constant current method of operation but not for the constant voltage method. Also, the change in resistance of the resistance exposed to the sample gas must be a linear function of the thermal conductivity of the gas mixture in the sample cavity. In general, this relationship is not linear and only becomes approximately linear when the change in resistance of the resistance exposed to the sample gas is very small compared to the resistance exposed to the reference gas and the number of sample gas molecules is negligible compared to the number of reference gas molecules. Finally, the thermal conductivity of the gas mixture must be a linear function of the sample concentration and again, this relationship is generally not linear. Again, only for a small number of sample molecules compared to the number of reference gas molecules, does this relationship reduce to an approximate linear relationship. Thus, at sample concentrations above ten percent, the output signal is a non-linear result of sample concentration causing a loss in detector sensitivity.

Prior solutions to this non-linearity problem have been limited to the use of calibration curves for each sample tested, otherwise, the thermal conductivity detector method could not be used for high sample concentrations.

SUMMARY OF THE PRESENT INVENTION

It is therefore an object of the present invention to provide an improved thermal conductivity detector power supply capable of precisely controlling the linearity of the output response at high sample concentrations.

It is a further object to provide an improved detector power supply capable of precisely controlling the linearity of the output response when the reference gas has a higher thermal conductivity than the sample gas.

It is a further object to provide improved thermal conductivity detector sensitivity at high sample concentrations by incorporating a power supply that can be used to drive conventional detector cells.

Briefly, a preferred embodiment of the present invention includes a voltage power supply, a voltage-to-current operational amplifier with associated feedback circuitry, and a four element thermal conductivity detector. In accordance with the illustrated embodiment, the power supply provides an electrical current to the thermal conductivity detector. As sample gas concentration increases, the operational amplifier feedback circuit responds to the resulting variations in the detector bridge impedance such that the electrical current supplied to the detector is varied to compensate for these changes in the detector bridge impedance. This feedback circuit action permits the bridge detector to operate linearly at high sample concentrations.

An advantage of the thermal conductivity detector power supply of the present invention is that the linearity of the output response is precisely controlled at high sample concentrations.

A further advantage of the detector power supply is that the linearity of the output response is precisely controlled when the reference gas has a higher thermal conductivity than the sample gas.

Another advantage is that the thermal conductivity detector sensitivity is improved at high sample concentrations and the power supply can be used to drive conventional detector cells.

These and other objects and advantages of the present invention will no doubt become obvious to those of ordinary skill in the art after having read the following detailed description of the preferred embodiment which is illustrated in the various drawing figures.

IN THE DRAWING

FIG. 1 is a circuit diagram of a conductivity detector and power supply;

FIG. 2 is a detailed circuit diagram of the thermal conductivity detector of the present invention with a voltage-to-current converter with feedback circuitry;

FIG. 3 is a graph of detector sensitivity and detector current characteristics versus percent sample gas concentration of a detector in accordance with the present invention as illustrated in FIG. 2; and FIG. 4 is a graph of thermal conductivity detector bridge output in volts versus butane sample concentration in (ppm) at various detector operating current levels of a detector in accordance with the present invention as illustrated in FIG. 2.

DETAILED DESCRIPTION OF THE PREFERRED EMBODIMENT

FIG. 1 illustrates a block diagram representation of a power supply referred to by the general reference character 10 and a thermal conductivity detector referred to by the general reference character 12. The detector 12 is positioned within a thermal conductivity detector chamber 14, illustrated by the broken line block. The power supply 10 includes electronic circuitry that is described in detail in FIG. 2.

The detector 12 includes a plurality of resistance filaments 16, 18, 20, and 22 connected as a bridge. Any voltage imbalance $E_0$ of the bridge may be detected between a pair of nodes 24 and 26. The node 24 is common to the filaments 20 and 22 and the node 26 is common to the filaments 16 and 18. The elements 16 and 22 are joined at a common node 28 and the elements 18 and 20 are connected at a common node 29. An equivalent load resistance ($R_L$) of the detector bridge 12 is shown skematically by resistance 30 connected across nodes 28 and 29. A pair of terminals 32 to measure any voltage imbalance $E_0$ are connected to nodes 24 and 26. A line 34 interconnects the power supply 10 with the detector 12.

When no gas sample is present in the thermal conductivity detector chamber 14, each resistance filament 16, 18, 20 and 22 is exposed only to a reference gas. Under these conditions, all gas within the chamber 14 has a fixed thermal conductivity and thus removes heat from each resistance filament 16, 18, 20 and 22 at the same rate. Thus, the resistance of each resistance filament 16, 18, 20 and 22 varies at the same rate permitting current I on the line 34 connected to the power supply 10 to divide evenly within each leg of the bridge of the detector 12. Therefore, no voltage imbalance Eo exists across the terminals 32. When a sample gas (SAM) is introduced into the detector chamber 14, two of the resistance filaments 16 and 20 are exposed to a mixture of samples gas (SAM) and reference gas (REF). Because the sample gas (SAM) has a lower thermal conductivity than the reference gas (REF), the mixture of gases has a thermal conductivity lower than that of the reference gas. Then, as current (I) on line 34 flows through detector 12, the electrical heat produced in filaments 16 and 20 is not dissipated as rapidly as that in filaments 18 and 22. Therefore, the resistance of filaments 16 and 20 increase by a differential resistance $\Delta R_1$ and $\Delta R_2$ respectively, causing a voltage imbalance $E_O$ across terminal 32. This output voltage imbalance $E_0$ is the detector output signal and becomes non-linear at sample gas concentrations greater than ten percent. As the sample concentration increases, the differential resistances $\Delta R_1$ and $\Delta R_2$ cause the current (I) on line 34 to decrease, thereby reducing the detector 12 sensitivity. At this point, the power supply 10 senses a decrease in current (I) on the line 34 and compensates for the increase in differential resistances by adjusting the value of current (I) on line 34.

Now, referring to FIG. 2, there is illustrated a circuit diagram of the electronic power supply 10. The electronic power supply 10 includes a voltage source 40, a voltage-to-current converter consisting of a differential sensing means in the form of an operational amplifier 42 with differential input terminals 44 and 46, a parameter sensing means in the form of a current sensing resistor 48, and feedback means in the form of a pair of feedback resistors 50 and 52 of equal value. The amplifier input terminals 44 and 46 are each electrically connected to a source output means in the form of an input resistor 54 and 56, respectively.

Electrically the detector 12 appears to power supply 10 as the equivalent load resistance ($R_L$) 30 which is equal to the reference resistance R plus one-half of the differential resistance $\Delta R_1$. Although there are two differential resistances, i.e., $\Delta R_1$ and $\Delta R_2$, only one is discussed for illustration purposes. When current (I) on line 34 varies because the differential resistance $\Delta R_1$ has varied, the power supply 10 adjusts current (I) on line 34 in the following manner.

In the dynamic current drive method, the detector bridge circuit 12 is driven by the electronic power supply 10 which provides current (I) on line 34 as a weak function of $\Delta R_1$. Consequently, when $\Delta R_1$ becomes large due to the presence of a high concentration of sample gas (SAM), power supply 10 provides a small change in current (I) on line 34 to compensate for the loss in detector 12 sensitivity that would otherwise occur. The key element in this dynamic current drive method is the fundamental relationship between the current (I) on line 34 and the differential resistance $\Delta R_1$ expressed as $$I = (C_1)(1 - C_2 R_L)^{-1}. \tag{1}$$

In this equation, $R_L = R + \Delta R_{\frac{1}{2}}$ where R is the reference resistance of filament 18 and $\Delta R_1$ is the differential resistance of filament 16. Also $C_1$ and $C_2$ are constants whose magnitude are determined empirically to provide optimum linear response for the specific detector cell 12 used. In effect, the detector cell 12 is used as a sensor to indicate by the magnitude of differential resistance $\Delta R_1$ when a change in current (I) on line 34 is needed to compensate for a loss in detector 12 sensitivitiy. To achieve this, amplifier 42 and resistances 48, 50, 52, 54, and 56 function to convert the voltage 40 into current (I) on line 34 that is supplied to the equivalent load resistance 30. The values of these fixed resistance elements 48, 50, 52, 54, and 56 determine the functional dependence of current (I) on line 34 to resistance 30.

In the preferred embodiment of this circuit, $R_{56}=R_{54}+R_0$ where $R_{56}$ equals resistance of element 56, $R_{54}$ equals resistance element 54, and $R_0$ represents the magnitude by which resistance element 56 exceeds resistance element 54. In addition, the resistance of both elements 50 and 52 are much less than the resistance of element 48. Under these conditions, current (I) on line 34 is related to the voltage of the source 40 and load resistance ($R_L$) 30 according to the following equation:

$$I = \frac{VR_{52}}{\left(1 + \frac{R_0}{R_{54}+R_{52}}\right) R_{48}R_{54} - \left(1 - \frac{R_{54}}{R_{54}+R_{52}}\right) R_0 R_L} \quad (2)$$

In equation 2, the term involving load resistance 30 drops out if $R_0=0$ so that current (I) on line 34 is then independent of load resistance 30. This is the condition for a conventional type constant current power supply.

In the present invention, a dynamic current drive power supply 10 is obtained by having $R_0$ not equal to zero. It is this difference, between resistance elements 54 and 56, which allows the classical constant current source to operate as a load dependent non-constant source as demonstrated by equation (2). Thus if $R_0$ has a positive value, then current (I) on line 34 is a positive function of load resistance 30 and current (I) on line 34 increases when load resistance 30 increases. If $R_0$ has a negative value, then current (I) is a negative function of the load resistance 30 and the current (I) on line 34 increases when the load resistance 30 decreases.

Specifically, source 40 applies a potential difference across the amplifier input terminals 44 and 46. Under constant load conditions, current (I) on line 34 is a fixed value, since resistor 48 acts as a current sensor. Note, feedback resistor 52 is connected to the input node 58 of resistor 48, and feedback resistor 50 is connected at the output node 60 of resistor 48 and a current on line 62 flowing through resistor 48 creates a potential proportional to resistance 48. A feedback current on line 64 passing through feedback resistor 52 and a feedback current on line 66 passing through feedback resistor 50 create potentials proportional to the potential across resistor 48. Thus, the potential across resistor 48 is also impressed across amplifier inputs 44 and 46. For a fixed load resistance 30 across the detector 12, the feedback to amplifier 42 remains constant. Note, the polarity of the feedback to terminals 44 and 46 of amplifier 42 opposes the polarity of the potential difference across amplifier inputs 44 and 46 from voltage source 40. Under these conditions, no potential difference appears at input terminals 44 and 46 and the current (I) on line 34 to the load resistor 30 remains at some constant value.

When the sample gas (SAM) concentration increases, the equivalent load resistance 30 increases and current (I) on line 34 decreases as previously described in FIG. 1. Since resistance 30 appears larger to amplifier 42, current (I) on line 34 becomes smaller causing the potential developed across resistance 48 to become smaller. Therefore, the potential developed across amplifier inputs 44 and 46 from feedback, when resistance 30 is increased by differential resistances $\Delta R_1$ and $\Delta R_2$ is smaller than the potential difference developed across amplifier inputs 44 and 46 from feedback when resistance 30 is not increased by differential resistances $\Delta R_1$ and $\Delta R_2$. Since this potential difference developed across amplifier inputs 44 and 46 from feedback is smaller and since its polarity opposes the polarity of the potential difference developed across amplifier inputs 44 and 46 from voltage source 40, the resultant potential difference developed across amplifier inputs 44 and 46 when resistance 30 increases, is larger. This causes amplifier 42 to increase current (I) on line 34 in response to the increase in the load resistance 30 by differential resistances $\Delta R_1$ and $\Delta R_2$ and to remain constant until the differential resistances $\Delta R_1$ and $\Delta R_2$ vary again. It is significant that the voltage developed across resistance 48 gets impressed through the feedback resistances 50 and 52, causing amplifier 42 to drive harder until input differential voltage equilibrium is achieved. Thus, the sensitivity of detector 12 is restored and the detector voltage imbalance $E_0$ across terminals 32 remains linear with increasing sample gas concentration.

As an example of a device constructed according to the present invention, the following values of resistances have been used: $R_0=320$, $R_{54}=5k$, $R_{52}=10k$, and $R_{48}=10$ ohms. With V representing the voltage of the source 40, and these resistance values, the relationship between I, V, and $R_L$ becomes the following:

$$I = \frac{0.20V}{(1 - 4.2 \times 10^{-3} R_L)} \quad (3)$$

Equation (3) represents a current I which is a weak, positive function of $R_L=R+\Delta R/2$. The specific numerical coefficient $4.2 \times 10^{-3}$ was determined empirically by selecting the value of $R_0$ which produced the optimum linear response for the thermal conductive detector (TCD) cell used. For this empirical determination, the TCD cell used was a four-filament, Model 10-952 cell manufactured by Gow Mac Instrument Co. of Bound Brook, N.J. The filaments in this cell were composed of a tunsten-rhenium alloy and their resistance (R) varied with temperature according to the following equation:

$$R = 29.6 + 0.0963T, \quad (4)$$

with R in ohms and T in °C.

In a typical operation, the TCD cell is heated by external means to a detector cell block temperature usually between 100°–400° C. Reference gas is supplied to both sample and reference chambers of the TCD cell and an appropriate voltage is selected to supply the TCD filaments with a current determined according to equation (3). With samples introduced to the TCD gas stream, the filaments exposed to the sample increase their resistance by the amount $\Delta R$ compared to the filaments exposed to the reference gas. At large concentrations of sample, the magnitude of $\Delta R$ becomes large enough to cause a corresponding small increase in I. This may be illustrated by again referring to equation (3) and substituting $R+\Delta R/2$ for $R_L$ whereby $$I = \frac{0.20V}{1 - (4.2 \times 10^{-3})\left(R + \frac{\Delta R}{2}\right)} \quad (5)$$

FIG. 3 graphically illustrates the operating characteristics of a thermal conductivity detector of the present invention. The graphic illustration includes a plot "A" of detector sensitivity versus percent butane concentration in helium using a constant current supply, a plot "B" of detector sensitivity versus percent butane concentration in helium using a dynamic current drive method incorporated in the present invention, and a plot "C" of current supplied to the thermal conductivity detector versus percent butane concentration in helium and percent change in current supplied to the detector. Sensitivity is defined as the ratio of output voltage imbalance ($E_0$) divided by sample concentration. In graphs of this type, linearity of detector response is represented by data that fit a horizontal line. The plot "A" shows that the constant current method data began deviating from linearity at a butane concentration of approximately ten percent. However, the plot "B" illustrates that data obtained with the dynamic current drive method of operation are linear to one hundred percent concentration of butane. The plot "C" illustrates the change in current supplied to the detector when the dynamic current drive method is used. At low butane concentration, a fixed current is supplied to the detector but at sample butane concentrations above ten percent, the current supplied to the detector increases to compensate for the loss in sensitivity that would otherwise occur. From the vertical scale entitled percent change in current of plot "C", note that an increase of only three to four percent in current is sufficient to provide linearity of response to one hundred percent sample concentration.

FIG. 4 graphically illustrates the operating characteristics of a thermal conductivity detector incorporating the present invention. The graphic illustration includes a plot of detector bridge output voltage imbalance $E_0$ versus butane sample concentration in parts-per-million for two currents supplied to the detector. Plot "D" illustrates the linear characteristics experienced at 150 milliamps supplied to the detector and plot "E" illustrates the same characteristic at 300 milliamps supplied to the detector. In both cases, the output voltage imbalance $E_0$ which is the measure of the change in composition of the gas stream, is directly proportional to the percent sample concentration.

Referring again to FIG. 2 and equation 2, current (I) on line 34 is a positive function of differential resistance $R_1$. This is the preferred embodiment of the present invention for the case in which the sample gas (SAM) has a lower thermal conductivity than the reference gas (REF). For the less frequent case in which the sample gas (SAM) has a higher thermal conductivity than the reference gas (REF), a first alternative embodiment of the present invention is disclosed. In this first alternative embodiment, $R_0$ assumes negative values in equation (2) such that $R_{56}$ is smaller than $R_{54}$ in the relation $R_{56} = R_{54} + R_0$. This causes a negative functional relationship between current (I) on line 34 and differential resistance $R_1$ such that when equivalent load resistance 30 decreases, the current (I) on line 34 increases.

In order to avoid excessively high filament temperatures, it is common practice to limit the maximum allowable filament temperature by decreasing the current (I) on line 34 supplied to the detector filaments 16, 18, 20, and 22 when the filament resistances reach a predetermined level. Accordingly, a second alternative embodiment of the present invention is the combination of the power supply 10 and detector 12 of FIG. 2 with another circuit that limits the load resistance 30 to some predetermined maximum value.

In summary, the present invention provides a thermal conductivity detector of improved linear response and sensitivity at high sample concentrations by providing a current supply to the detector that is dependent upon the change in the detector filament resistance that is exposed to the sample gas. The dynamic current drive method of operation provides a means of improving by at least a factor of ten the linear response of the detector at high sample concentration. A detector incorporating this dynamic current drive method has no upper limit of linear response which is unique among gas chromatography detectors.

Although the present invention has been described in terms of the presently preferred and alternative embodiments, it is to be understood that such disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true spirit and scope of the invention.

We claim:

1. Apparatus for maintaining sensitivity and response linearity of a gas detection device, comprising in combination:

an electrical energy source means coupled to a first input terminal of a differential sensing means through a first source output means for providing a first parameter to said differential sensing means, a second source output means connected between said source means and a second input terminal of said differential sensing means for providing a second parameter to said differential sensing means, the differential sensing means including an output terminal, a first feedback means connected between said output terminal of the differential sensing means and said first input terminal of the differential sensing means for providing a first feedback parameter, a parameter sensing means coupled to said output terminal of said differential sensing means for developing an electrical voltage parameter responsive to the magnitude of an electrical current parameter provided by the differential sensing means; a second feedback means connected between an output terminal of said parameter sensing means and said second input terminal of the differential sensing means for providing a second feedback parameter; and detection means coupled to said output terminal of said parameter sensing means and to the source means for monitoring deviations in a voltage output parameter responsive to variations in a detection means current parameter and a differential resistance of the detection means, said detection means current parameter being weakly dependent upon said differential resistance of the detection means, said voltage output parameter being linearly dependent upon a sample gas concentration to at least one-hundred percent of said sample gas concentration for opposing a reduction in sensitivity of the detection means, said reduction in sensitivity being defined as a ratio of said voltage output parameter to said sample gas concentration, the magnitude of increase of said differential resistance being determinative of when an increase in said detection means current parameter and an increase in temperature of the detection means is required for opposing said reduction in sensitivity, said detection means current parameter being increased in magnitude when said sample gas concentration exceeds ten-percent and said sample gas having a lower thermal conductivity than a reference gas supplied to said detection means.

2. The apparatus of claim 1 wherein the electrical energy source means comprises a voltage source for providing a source current to each of said first source and said second source output means for developing said first and said second parameter.

3. The apparatus of claim 1 wherein the first source output means comprises a first electrical resistance path for providing said first parameter, said first parameter being summed with said first feedback parameter to provide a first differential parameter to said sensing means.

4. The apparatus of claim 3 wherein the second source output means comprises a second electrical resistance path for providing said second parameter, the resistance of said second electrical resistance path being greater in magnitude than the resistance of said first electrical resistance path by a resistance $R_0$, said resistance $R_0$ being nonzero and having a magnitude much smaller than the magnitude of the resistance of said first electrical resistance path, said second parameter being greater in magnitude than said first parameter, said resistance $R_0$ for operating said electrical energy source means as a load dependent, non-constant current source, said second parameter being summed with said second feedback parameter to provide a second differential parameter to said sensing means.

5. The apparatus of claim 4 wherein the first feedback means and the second feedback means comprise a pair of equal resistance paths, said resistance path of the first feedback means extending between said output terminal of said differential sensing means and said first input terminal of the differential sensing means and said resistance path of the second feedback means extending between said output terminal of the parameter sensing means and said second input terminal of the differential sensing means.

6. The apparatus of claim 5 wherein the first input terminal of the differential sensing means and the second input terminal of the differential sensing means collectively comprise a junction for differentially summing said first and said second differential parameters.

7. The apparatus of claim 6 wherein the differential sensing means comprises a voltage-to-current operational amplifier.

8. The apparatus of claim 7 wherein the parameter sensing means comprises an electrical resistance path for providing a potential difference proportional to the magnitude of said electrical current parameter of the differential sensing means said electrical current parameter comprising a first feedback current flowing through said first feedback means for providing said first feedback parameter and a second feedback current flowing through said second feedback means for providing said second feedback parameter.

9. The apparatus of claim 8 wherein the detection means comprises a thermal conductivity detector which identifies concentration changes within gas streams and wherein said differential resistance of the detection means is a change in electrical resistance of at least two resistors in a wheatstone bridge located within said detection means, said differential resistance being provided by said change in electrical resistance responsive to said sample gas concentration and wherein said output voltage parameter being an output voltage imbalance of said wheatstone bridge responsive to variations in said detection means current parameter.

10. A method for maintaining sensitivity and response linearity of a gas detection device, said method comprising the steps of:
providing an electrical source for energizing a gas detection device;
providing a first resistance path responsive to said electrical source for providing a first electrical parameter;
providing a second resistance path responsive to said electrical source for providing a second electrical parameter;
providing a third resistance path in electrical communication with said first resistance path for providing a first feedback parameter;
providing a fourth resistance path in electrical communication with said second resistance path for providing a second feedback parameter;
summing said first electrical parameter and said first feedback parameter responsive to said electrical communication between said first resistance path and said third resistance path for providing a first differential parameter;
summing said second electrical parameter and said second feedback parameter responsive to said electrical communication between said second resistance path and said fourth resistance path for providing a second differential parameter;
subtracting said first differential parameter from said second differential parameter responsive to said first electrical parameter summed to said first feedback parameter and said second electrical parameter summed to said second feedback parameter for providing a differential input parameter; converting and amplifying said differential input parameter responsive to the difference between said first and said second differential parameters for providing a third electrical parameter;
sensing the existence of said third electrical parameter responsive to converting said difference between said first and said second differential parameters to said third electrical parameter for developing a fourth electrical parameter;
measuring the magnitude of said fourth electrical parameter for providing said first and said second feedback parameters; and
monitoring variations in a fifth electrical parameter and deviations of said third electrical parameter, said fifth electrical parameter being monitored in said gas detection device, said gas detection device receiving said third electrical parameter and wherein said variations in said fifth electrical parameter being provided by fluctuations in a concentration of a sample gas within said gas detection device, said variations in said fifth electrical parameter providing said deviations in said third electrical parameter and providing and detecting an output parameter, said output parameter being a linear indication of said fluctuation in said sample gas concentration within said gas detection device, said first and said second feedback parameters sensing said deviations in said third electrical parameter and detecting said output parameter for providing said differential input parameter for adjusting said third electrical parameter in response to said variations in said fifth electrical parameter for maintaining sensitivity and response linearity of said gas detection device.

11. The method of claim 10 wherein the electrical source comprises a voltage source for energizing the detection device.

12. The method of claim 11 wherein said first electrical parameter comprises a first potential difference developed across a first electrical resistor in electrical communication with the voltage source.

13. The method of claim 12 wherein said second electrical parameter comprises a second potential difference developed across a second electrical resistor in electrical communication with the voltage source and unequal to said first potential difference.

14. The method of claim 13 wherein said first feedback parameter comprises a third potential difference responsive to the existance of said third electrical parameter.

15. The method of claim 14 wherein said second feedback parameter comprises a fourth potential difference responsive to the existance of said third electrical parameter.

16. The method of claim 15 wherein said first differential parameter comprises the differential sum of said first potential difference and said third potential difference.

17. The method of claim 16 wherein said second differential parameter comprises the differential sum of said second potential difference and said fourth potential difference.

18. The method of claim 17 wherein said differential input parameter comprises the difference between the sum of said first and said third potential differences from the sum of said second and said fourth potential differences.

19. The method of claim 18 wherein said third electrical parameter comprises an electric current responsive to converting said differential input parameter from a potential difference to an electrical current.

20. The method of claim 19 wherein said fourth electrical parameter comprises a fifth potential difference and wherein increments of said fifth potential difference provide said first and said second feedback parameters.

21. The method of claim 20 wherein said fifth electrical parameter comprises a sensitive resistive element within the gas detection device and wherein said output parameter comprises a sixth potential difference for indicating a variation in said sensitive resistive element.

22. The apparatus of claim 9 wherein an increase in said sample gas concentration provides said differential resistance, said differential resistance increasing an equivalent resistance of the detection means and initially decreasing said potential difference developed across said electrical resistance path of the parameter sensing means, said first and said second feedback current being reduced in magnitude providing a smaller first and second feedback parameter to be summed respectively with said first and said second parameters, said first and said second feedback parameters each being a feedback potential difference and being smaller for increased sample gas concentration and opposite in polarity to a potential difference provided by each of said first and said second parameters wherein said first and said second differential parameters fed to said first and said second input terminals of the differential sensing means are increased in magnitude for providing an increase in magnitude of said electrical current parameter, and said detection means current parameter and the temperature of said detection means, said electrical current parameter and said detection means current parameter being constant until said differential resistance varies and wherein said feedback potential difference developed by each of said first and said second feedback parameters are impressed onto said first and said second input terminals of the differential sensing means for providing a differential voltage equilibrium for restoring the sensitivity of the detection means and for providing linearity of said voltage output parameter with said increasing sample gas concentration, said detection means current parameter being weakly and positively dependent upon said differential resistance and increasing when said differential resistance increases, the temperature of said detection means being controlled by a limiting circuit.

23. Apparatus for maintaining sensitivity and response linearity of a gas detection device, comprising in combination:
  an electrical energy source means coupled to a first input terminal of a differential sensing means through a first source output means for providing a first parameter to said differential sensing means;
  a second source output means connected between said source means and a second input terminal of said differential sensing means for providing a second parameter to said differential sensing means, the differential sensing means including an output terminal;
  a first feedback means connected between said output terminal of the differential sensing means and said first input terminal of the differential sensing means for providing a first feedback parameter;
  a parameter sensing means coupled to said output terminal of said differential sensing means for developing an electric voltage parameter responsive to the magnitude of an electrical current parameter provided by the differential sensing means;
  a second feedback means connected between an output terminal of said parameter sensing means and said second input terminal of the differential sensing means for providing a second feedback parameter; and
  detection means coupled to said output terminal of said parameter sensing means and to the source means for monitoring deviations in a voltage output parameter responsive to variations in a detection means current parameter and a differential resistance of the detection means, said detection means current parameter being weakly dependent upon said differential resistance of the detection means, said voltage output parameter being linearly dependent upon a sample gas concentration to at least one hundred percent of said sample gas concentration for opposing a reduction in sensitivity of the detection means, said reduction in sensitivity being defined as a ratio of said voltage output parameter to said sample gas concentration, the magnitude of decrease of said differential resistance being determinative of when an increase in said detection means current parameter and an increase in temperature of the detection means is required for opposing said reduction in sensitivity, said sample gas having a higher thermal conductivity than a reference gas supplied to said detection means and wherein the first source output means comprises a first electrical resistance path for providing said first parameter and the second source output means comprises a second electrical resistance path for providing said second parameter, the resistance of said second electrical resistance path being less in magnitude than the resistance of said first electrical resistance path by a resistance $R_0$, said resistance $R_0$ being nonzero and having a magnitude much smaller than the magnitude of the resistance of said first electrical resistance path, said second parameter being smaller in magnitude than said first parameter, said resistance $R_0$ for operating said electrical energy source means as a load dependent, non-constant current source, said first parameter being summed with said first feedback parameter and said second parameter being summed with said second feedback parameter for respectively providing a first differential parameter and a second differential parameter to said differential sensing means.

24. The apparatus of claim 23 wherein an increase in said sample gas concentration provides said differential resistance, said differential resistance increasing an equivalent resistance of the detection means and decreasing said potential difference developed across said electrical resistance path of the parameter sensing means, said first and said second feedback current being reduced in magnitude providing a smaller first and second feedback parameter to be summed respectively with said first and said second parameters, said first and said second feedback parameters each being a feedback potential difference and being smaller for increased sample gas concentration and opposite in polarity to a potential difference provided by each of said first and said second parameters wherein said first and said second differential parameters fed to said first and said second input terminals of the differential sensing means are decreased in magnitude for providing a decrease in magnitude of said electrical current parameter, and said detection means current parameter and the temperature of said detector means, said electrical current parameter and said detection means current parameter being constant until said differential resistance varies and wherein said feedback potential difference developed by each of said first and said second feedback parameters are impressed onto said first and said second input terminals of the differential sensing means for providing a differential voltage equilibrium for restoring the sensitivity of the detection means and for providing linearity of said voltage output parameter with said increasing sample gas concentration, said detection means current parameter being weakly and negatively dependent upon said differential resistance and decreasing when said differential resistance increases, the temperature of said detection means being controlled by a limiting circuit.

* * * * *